United States Patent
Decker

(10) Patent No.: US 9,586,866 B2
(45) Date of Patent: Mar. 7, 2017

(54) REFRACTORY COMPOSITION AND PROCESS FOR FORMING ARTICLE THEREFROM

(71) Applicant: Jens Decker, Ann Arbor, MI (US)

(72) Inventor: Jens Decker, Ann Arbor, MI (US)

(73) Assignee: Stellar Materials Incorporated, Boca Raton, FL (US)

(*) Notice: Subject to any disclaimer, the term of this patent is extended or adjusted under 35 U.S.C. 154(b) by 0 days.

(21) Appl. No.: 14/486,051

(22) Filed: Sep. 15, 2014

(65) Prior Publication Data

US 2016/0075604 A1 Mar. 17, 2016
US 2016/0236985 A9 Aug. 18, 2016

Related U.S. Application Data

(62) Division of application No. 13/636,968, filed as application No. PCT/US2011/029416 on Mar. 22, 2011, now abandoned.

(60) Provisional application No. 61/316,602, filed on Mar. 23, 2010.

(51) Int. Cl.

| C04B 28/34 | (2006.01) |
|---|---|
| C04B 35/447 | (2006.01) |
| C04B 33/04 | (2006.01) |
| C04B 12/02 | (2006.01) |
| C04B 35/101 | (2006.01) |
| C04B 35/14 | (2006.01) |
| C04B 35/185 | (2006.01) |
| C04B 35/565 | (2006.01) |
| C04B 35/626 | (2006.01) |
| C04B 35/63 | (2006.01) |
| C04B 35/634 | (2006.01) |
| C04B 35/66 | (2006.01) |
| C04B 35/76 | (2006.01) |
| C04B 33/32 | (2006.01) |
| C04B 35/10 | (2006.01) |
| C04B 35/657 | (2006.01) |
| C04B 111/00 | (2006.01) |
| C04B 111/28 | (2006.01) |

(52) U.S. Cl.

CPC ............ *C04B 33/04* (2013.01); *C04B 12/022* (2013.01); *C04B 12/027* (2013.01); *C04B 28/34* (2013.01); *C04B 33/32* (2013.01); *C04B 35/10* (2013.01); *C04B 35/101* (2013.01); *C04B 35/14* (2013.01); *C04B 35/185* (2013.01); *C04B 35/565* (2013.01); *C04B 35/6263* (2013.01); *C04B 35/62665* (2013.01); *C04B 35/6309* (2013.01); *C04B 35/63488* (2013.01); *C04B 35/657* (2013.01); *C04B 35/66* (2013.01); *C04B 35/76* (2013.01); *C04B 2111/00431* (2013.01); *C04B 2111/28* (2013.01); *C04B 2235/3201* (2013.01); *C04B 2235/3208* (2013.01); *C04B 2235/3217* (2013.01); *C04B 2235/3222* (2013.01); *C04B 2235/3427* (2013.01); *C04B 2235/447* (2013.01); *C04B 2235/48* (2013.01); *C04B 2235/524* (2013.01); *C04B 2235/6027* (2013.01); *C04B 2235/656* (2013.01); *C04B 2235/77* (2013.01); *C04B 2235/96* (2013.01); *C04B 2235/9615* (2013.01); *Y02W 30/94* (2015.05)

(58) Field of Classification Search
CPC ..... C04B 28/34; C04B 28/342; C04B 28/344; C04B 28/348; C04B 35/10; C04B 35/565; C04B 35/14
See application file for complete search history.

(56) References Cited

U.S. PATENT DOCUMENTS

| 4,040,809 | A | | 8/1977 | Pecoraro et al. |
|---|---|---|---|---|
| 4,659,690 | A | | 4/1987 | McDaniel et al. |
| 4,806,168 | A | * | 2/1989 | Ivarsson ................. C04B 28/00 106/644 |
| 5,707,442 | A | | 1/1998 | Fogel et al. |
| 5,900,382 | A | | 5/1999 | Shaw |
| 6,258,742 | B1 | * | 7/2001 | Carini ................ B22D 11/0405 501/127 |
| 6,267,066 | B1 | | 7/2001 | Schickling et al. |
| 6,740,299 | B2 | * | 5/2004 | Carini ................... C04B 28/342 423/311 |
| 2003/0003039 | A1 | | 1/2003 | Carini et al. |
| 2012/0304904 | A1 | | 12/2012 | Decker et al. |
| 2013/0210605 | A1 | * | 8/2013 | Decker .............. A61K 38/1709 501/89 |

FOREIGN PATENT DOCUMENTS

| CN | 102603316 | * | 7/2012 |
|---|---|---|---|
| JP | 03205372 | * | 9/1991 |
| JP | 05004874 | B2 | 8/2012 |

* cited by examiner

*Primary Examiner* — Karl Group
(74) *Attorney, Agent, or Firm* — Dinsmore & Shohl LLP; Weston Gould

(57) ABSTRACT

A refractory composition and processes for manufacture are provided where the compositions possess improved refractory alkali resistance and superior handling properties. Compositions and processes for their manufacture may include a plurality of ceramic particles and a binder sintered to the particles wherein the binder includes crystalline aluminum orthophosphate distributed as the result of an in situ reaction of aluminum metaphosphate with alumina. Kits provided according to the invention provide materials for use in manufacture of a composition where the kit includes aluminum metaphosphate and a nonfacile additive.

7 Claims, No Drawings

REFRACTORY COMPOSITION AND PROCESS FOR FORMING ARTICLE THEREFROM

CROSS REFERENCE TO RELATED APPLICATIONS

This application is a divisional of U.S. application Ser. No. 13/636,968, filed Nov. 9, 2012 (abandoned), which is a National Stage Application of PCT/US2011/029416 filed Mar. 22, 2011, which depends from and claims priority to U.S. Provisional Application No. 61/316,602 filed Mar. 23, 2010.

FIELD OF THE INVENTION

The present invention in general relates to a refractory composition and process for forming an article therefrom, and in particular a composition having crystalline $AlPO_4$ formed in the composition binder alone or with other binder components to produce an article with exceptional refractory corrosion resistance.

BACKGROUND OF THE INVENTION

Cement bonded materials largely form only mechanical bonds at ambient temperature of 20° Celsius. Adhesion of these ambient temperature cured materials occurs because of the rough surface and while convenient to bond at ambient temperature are comparatively weak as compared to elevated temperature cured material and also tend to suffer from mechanical failure during heat up or when exposed to thermal stresses. Representative of such materials are THERMBOND® refractories that are characterized by chemically bonding both to the cement components and to existing substrates. During the exothermic reaction between dry aggregate and a liquid activator, ionic bonding occurs to form metal-oxide phosphates to provide both coherence and adherence to impart greater strength and durability in chemically aggressive high temperature environments. This material is characterized by a binder system inclusive of alkali phosphates to facilitate ambient temperature set and bonding. Unfortunately, alkali phosphates are characterized by low melting points that limit the high temperature limit of operation for the resulting material. Additionally, the acidity of alkali phosphates precludes introduction of a variety of dispersing or deflocculating agents that otherwise could improve handling properties of the precured cement mixture. As a result, cement strengthening through densification is largely precluded as are often desirable handling methods such as pumping or shotcreting unless extra phosphoric acid is added to improve precured cement mixture flowability and extend working times. However, the addition of more phosphoric acid alters the phosphate:alkali ratio in the precured cement mixture and thereby invariably reduces the strength properties of cement formed with extra phosphoric acid relative to a cast precured cement mixture lacking additional phosphoric acid. As a result of these limitations, alkali phosphate binder system based refractory cements have met with limited acceptance.

Thus, there exists a need for a refractory composition inclusive of a phosphate binder with improved refractory alkali resistance and superior handling properties. There also exists a need for refractory articles formed from such a composition that have an extended operational lifetime relative to conventional refractory articles.

SUMMARY OF THE INVENTION

Refractory compositions and kits and processes for forming inventive refractory compositions are provided that overcome the shortcomings of refractory materials of the prior art and improve handling characteristics and article strength. A refractory composition includes a plurality of aggregate ceramic particles and a binder sintered to the plurality of aggregate ceramic particles, where the binder includes crystalline aluminum orthophosphate distributed in the binder as the result of reaction of aluminum metaphosphate with alumina. The plurality of aggregate ceramic particles optionally include bauxite particles. In some embodiments, the plurality of aggregate ceramic particles includes at least one of silicon carbide, fumed silica, or mullite.

The crystalline aluminum orthophosphate optionally has a crystal structure of berlinite. In some embodiments the crystalline aluminum orthophosphate is devoid of an amorphous glass phase.

The compositions according to the invention optionally include facile or nonfacile additives where a nonfacile additive is optionally calcium aluminate cement, sodium silicate, polyphosphate, or organic salts. Optionally, a composition includes steel fiber filler.

The unique compositions of the invention provide for increased strength relative to prior art refractory compositions where some embodiments of the invention have a density greater than or equal to 90% of theoretical and, optionally, a cold crush strength of greater than 100 $N/mm^2$.

Processes for forming a refractory article are also provided that include mixing aluminum metaphosphate particulate with $Al_{2-x}MO_3$ in the presence of less than 10 slurry weight percent of water or an organic solvent to form a mixture, and heating the mixture to a temperature and for a time sufficient to induce the reaction

$$Al(PO_3)_3 + Al_{2-x}MO_3 \rightarrow AlAl_{2-x}MPO_4 \quad (II)$$

where M is Sb, Bi, B, Cr (III), Er, Gd (III), In (III), Ni (III), Rh (III), Sm (III), Sc (III), Tb (III), Ti (III), W (III), V (III), Yb (III), or Y (III); and x is a number between 0 and 2, inclusive. In some embodiments the temperature used to induce the reaction is greater than 800° Celsius.

The process optionally further includes mixing a plurality of aggregate particles with said aluminum metaphosphate particulate and $Al_{2-x}MO_3$. Optionally, at least one additive of calcium aluminate cement, sodium silicate, or polyphosphate is added to the mixture prior to heating. A process optionally includes embedding steel fibers within the mixture.

A process optionally includes pouring the mixture into a mold having a shape complementary to an article and allowing the mixture to dry to form a piece of greenware, and heating the greenware to induce the reaction. A mold is optionally a plaster mold.

A kit is provided optionally for use in forming an inventive composition where the kit includes aluminum metaphosphate and a nonfacile additive. Instructions are optionally provided with the kit where the instructions are to combine aluminum metaphosphate with alumina and less than 10 slurry percent water or organic solvent for casting and then firing at a temperature above 800° Celsius to form aluminum orthophosphate as a continuous binder matrix phase.

A nonfacile additive optionally comprises calcium aluminate cement, sodium silicate, sodium polyphosphates, or combinations thereof. A kit optionally further includes a facile additive. In some embodiments, a kit includes steel fiber filler.

DETAILED DESCRIPTION OF THE INVENTION

The present invention has utility as a refractory composition inclusive of a variety of aggregate particles, fibers, and fillers joined by an in situ formed binder containing crystalline aluminum orthophosphate, $AlPO_4$. A common crystalline form of aluminum orthophosphate is berlinite. According to the present invention a kit is provided to produce a refractory binder. The kit includes aluminum metaphosphate, $Al(PO_3)_3$, calcium aluminate, along with instructions to mix the contents with a quantity of water and a source of refractory aggregate, and after set firing to form a refractory material. With the refractory aggregate containing alumina, $Al_2O_3$ the aluminum metaphosphate reacts to form crystalline aluminum orthophosphate, $AlPO_4$. Aluminum orthophosphate is the thermodynamic product upon heating to a temperature greater than about 580° Celsius with a decomposition temperature of about 1650° Celsius. The resultant refractory composition is amenable to incorporation of reinforcing materials such as steel fibers and is operative with aggregate particulate including silicon carbide, mullite, alumina, titania, and combinations thereof. Such a refractory composition is readily formed with a density of greater than 90%, a theoretical density and cold crush strengths in excess of 88 Newtons per square millimeter. Through control of water content and conventional additives, the cast form of an article from an inventive composition has sufficient green strength to be handled and optionally machined prior to firing to provide a refractory article with superior strength and alkali resistance, as compared to conventional materials.

An inventive bindery for a refractory material includes aluminum metaphosphate that is mixed aggregate ceramic particles and processed under conditions to afford aluminum orthophosphate as a crystalline binder. The binder aluminum orthophosphate has as a predominant phase berlinite. It is appreciated that aluminum metaphosphate as binder precursor is amenable to inclusion in a kit as aluminum metaphosphate is far less hygroscopic as compared to phosphoric acid, more pH neutral (around pH5) and is commercially available in a variety of particle mesh sizes. The reaction of aluminum metaphosphate with alumina (synonymously termed bauxite herein) to form a crystalline binder phase of aluminum orthophosphate (synonymously referred to herein as berlinite) is detailed with respect to the following equation:

$$Al(PO_3)_3 + Al_2O_3 \rightarrow 3AlPO_4 \qquad (I)$$

Aluminum orthophosphate appears to be a thermodynamically stable phase that is formed upon heating the reagents to a temperature above about 580° Celsius. Aluminum orthophosphate is noted to have a decomposition temperature of about 1650° Celsius at ambient pressure. It is appreciated that the formation temperature of aluminum orthophosphate varies according to predictable thermodynamic relationships when the reaction proceeds at pressures other than atmospheric pressure. It is appreciated that formation of a refractory composition according to the present invention readily occurs through firing the green form of an article through hot isostatic pressing (HIP). It is appreciated that a mixed metal orthophosphate is readily formed according to the reaction:

$$Al(PO_3)_3 + Al_{2-x}MO_3 \rightarrow AlAl_{2-x}MPO_4 \qquad (II)$$

where M is Sb, Bi, B, Cr (III), Er, Gd (III), In (III), Ni (III), Rh (III), Sm (III), Sc (III), Tb (III), Ti (III), W (III), V (III), Yb (III), or Y (III); and x is a number between 0 and 2, inclusive.

The resultant mixed metal orthophosphate produced according to Equation (II), in addition to being operative as a binder for a refractory composition, also is appreciated to be operative in catalytic and phosphor applications.

The amount of aluminum metaphosphate present to form a matrix around refractory ceramic particulate depends on factors including size of the ceramic particulate, desired interparticle separation, morphology, size of primary crystals and oxide state. Typically, aluminum metaphosphate is present between 2 and 20 total weight percent of the fully formulated refractory composition casting slurry. Preferably, alumina is present in excess of molar stoichiometry of alumina metaphosphate. It is appreciated that alumina is present as aggregate ceramic particles or alternatively is added as a minor quantity of the ceramic particles for reaction with the alumina metaphosphate.

To facilitate mixing of ceramic particle aggregate and alumina metaphosphate as a binder precursor, a quantity of water or organic solvent is added to afford a slurry of a desired viscosity. Such organic solvents illustratively include alcohols, ketones, esters, ethers, amides, amines, glycols, alkanes, and the like. Preferably such organic solvents are liquids below 200° Celsius and preferably are liquids at 20° Celsius. Typical loadings of water or solvents range from 2-20 total weight percent of a fully formulated refractory composition slurry. Optionally, additives are included that are consumed during berlinite formation, these additives provided to promote ease of handling. Such additives illustratively include surfactants; polymerizable organic monomers or oligomers, deflocculants; polymers; and organic acids such as citric, and oxalic. While one of ordinary skill in the art can readily adjust slurry viscosity and green strength through the inclusion of such additives, typically each such additive is present from 0.01-5 total weight percent of a fully formulated refractory composition slurry. It is appreciated that the inclusion of organic monomeric or oligomeric polymerizable materials that upon cure can improve the green strength of the composition prior to firing or reaction according to Equation (I) or (II). The resultant polymer is decomposed and therefore not present in the resultant refractory composition. Exemplary of such organic polymers are acrylic acids, acrylates, polyethylene glycols, and polycarboxylate ethers, which are added as polymeric precursors or slurry soluble preformed polymers.

Handling properties of an inventive refractory composition slurry and the green strength of an inventive composition form after drying are also modified through inclusion of nonfacile additives. While the amount of such nonfacile additives is controlled by factors including desired green strength, refractory composition, working environment, temperature and corrosivity, desired cold crush strength, and setting time, working time and curing time, typical loadings of such nonfacile additives range from 0.1 to 10 total weight percent of a fully formulated refractory composition slurry. Representative nonfacile additives operative herein include calcium aluminate cement, sodium silicate, fumed silica, alkali metal or alkali earth polyphosphates, and organic salts like citric, oxalic or nitric acids, calcium silicate cement, potassium silicate, lithium silicate. Preferably, nonfacile additive is present in a quantity such that the aluminum orthophosphate forms a continuous matrix phase.

Ceramic particle aggregate embedded within an aluminum orthophosphate binder according to the present invention is limited only by the desired properties of the resultant refractory composition and compatibility with aluminum orthophosphate binder. Operative ceramic particle aggregates in the present invention illustrative include bauxite, tabular alumina, mullite, silicon carbide, fused silica, rutile, and andalusite, sillimanite, magnesite, forsterite, kyanite, Mg spinell, and chromium oxide. Typical loadings of aggregate ceramic particles range from 50-95 weight percent of a fully formulated refractory composition slurry. Typical aggregate particle sizes range from 0.1 to 1000 microns. It is appreciated that the aggregate particles can be in a variety of forms including spherical, polyhedral, irregular, and combinations thereof.

An inventive formulation optionally includes strengthening fibers such as steel fibers as detailed in U.S. Pat. No. 4,366,255. Typical loadings of fibers are from 0 to 50 total weight percent of a refractory composition slurry. Other strengthening fiber fillers operative herein include carbon fibers with the recognition that firing occurs in a reducing atmosphere.

The present invention is further detailed with respect to the following nonlimiting examples. These examples are not intended to narrow or otherwise limit the scope of the appended claims.

Example 1

5% aluminum metaphosphate was mixed into bauxite aggregate along with 4½ total weight percent water and 0.1% polyethylene glycol having a molecular weight of more than 300 grams per mole. Upon drying and firing at 800° Celsius for 5 hours, a ceramic was obtained having a crystalline aluminum orthophosphate continuous binder matrix phase as determined by x-ray powder diffraction.

Example 2

The slurry of Example 1 was modified to include 5% by slurry weight calcium aluminate cement with comparable results.

Example 3

To the slurry of Example 2, dry sodium silicate was added to 0.015 total percent. An increase in green strength is noted and faster setting time that facilitated ease of demolding and also produced a crystalline aluminum orthophosphate matrix phase.

Example 4

To the slurry of Example 1, 0.015 total weight percent dry sodium silicate was added to achieve an increase in green strength without resort to the calcium aluminate cement per Example 3. A formulation containing 88 total slurry weight percent bauxite, 0.015% dry sodium silicate, 5% aluminum metaphosphate, 0.1% polyethylene glycol, and the remainder water. After firing at 800° Celsius, cold crush strength of 200 N/mm$^2$ was obtained. To determine the permanent linear change and the resultant refractory material, the slurry was fired at temperatures of 1100° Celsius, 1370° Celsius, and 1600° Celsius. Permanent linear change at 1100° Celsius was 0.0%, −0.2% shrinkage at 1370° Celsius, and −0.2% shrinkage at 1600° Celsius. The results confirm that the aluminum orthophosphate system does not create a significant melt phase.

Hot modulus of rupture tests were conducted on material fired at 800° Celsius. The hot modulus of rupture is as follows for the noted test temperatures: 815° Celsius (38 N/mm$^2$); 1100° Celsius (35 N/mm$^2$); and 1200° Celsius (22 N/mm$^2$).

The density of the material in four separate tests ranged between 181.7 and 183.1 pounds per cubic foot.

Examples 5-8

Slurries were formulated according to Table 1 along with 0.15% dry sodium silicate. Resulting slurries were self flowing and upon firing at 815° Celsius afforded the cold crush strengths provided in Table 1. The results for the material of Example 4 are provided for reference.

TABLE 1

Slurries and cold crush strengths (C.C.S. in N/mm$^2$ measured at 800° C.) for Examples 5-8. Amounts are expressed in weight percent of the slurry, with the exception of wt. % alumina as a weight percent of the base aggregate and any added calcined alumina.

| Exa. | Aggregate Base | Wt. % alumina within base aggregate | Fumed Silica | CaO Al$_2$O$_3$ Cement | Aluminium-Metaphos. | Calcined Alumina | H$_2$O % | Sodium Silicate | Polyeth-Gly | C.C.S 800° C. |
|---|---|---|---|---|---|---|---|---|---|---|
| 4 | Bauxite 70% | 88% Alumina | 5 | — | 5 | 20 | 4.5 | 0.015 | 0.1 | 220 |
| 5 | Mullite 67% | 70% Alumina | 5 | 3 | 5 | 20 | 6 | 0.015 | 0.1 | 150 |
| 6 | Tabular Alumina 72% | 95% Alumina | — | 3 | 5 | 20 | 6 | 0.015 | 0.1 | 125 |
| 7 | SiC 70% | 70% SiC | 8 | 3 | 5 | 14 | 5.5 | 0.015 | 0.1 | 110 |
| 8 | Fused Silica 65% | 70% SiO$_2$ | 5 | — | 5 | 20 | 6.5 | 0.015 | 0.1 | 50 |

Refractories are categorized based on the aggregate used and the chemical composition. The above table shows aggregate base minerals like "bauxite" or "mullite." Both minerals contain for instance a certain amount of alumina which is a criterion for the refractoriness of these minerals. Beside alumina as a mineral component from bauxite or mullite there is also additional alumina in the form of calcined alumina in the formulations to obtain flow characteristics and strengths—particularly hot-strengths and in addition to that there is alumina in aluminum-metaphosphate and calcium aluminate cement. In Example 4 the total alumina content adds up to 88% alumina. Fume silica is an additive that fills submicron pores and improves the flow characteristics and lowers the water content at the same time. It is almost 100% pure $SiO_2$. Example 8 contains 65% fused silica but the total $SiO_2$ content is 70% due to the 5% $SiO_2$ from fume silica.

Example 9

The slurry of Example 4 was cast in a plaster mold and also fired at 815° Celsius. The hot modulus of rupture, porosity and density results for casting performed in a plaster mold relative to a non-permeable acrylic mold as used in Example 4 are provided in Table 2.

TABLE 2

Plaster molded refractory properties and those of some slurry cast in an acrylic mold.

| Example 9 | | Example 4 |
|---|---|---|
| Porosity after 1500 F.: | 7% | compared to 12%-14% on a regular cast sample |
| HotMOR after 1500 F.: | 48 N/mm$^2$ | compared to 37 N/mm$^2$ on a regular cast sample |
| Density after 1500 F.: | 196 lbs/ft$^3$ | compared to 184 lbs/ft$^3$ on a regular cast material |

Based on these results, the composition of Example 4 was used in plaster mold slip casting to form abrasion plates for use in coal fired burners or boiler tubes; launder segments, tap out blocks, ladle slide gates for steel forging, wear plates for ladles and in launders, and wear segments in metal-containing vessels for aluminum, copper, zinc, lead, cast iron, or other materials. After a piece of greenware was removed from the plaster mold, the greenware had sufficient strength to be amenable to additional machining prior to firing. Additionally, owing to the low water content compared to conventional plaster mold slip casting, shrinkage between a mold form and the fired article was minimal. Drying at 105° Celsius to volatilize water from the slurry prior to firing occurred. A molding was fast fired and noted to have a green strength of 33 N/mm$^2$ after drying at 104° Celsius: 63 N/mm$^2$ and after firing at 815° Celsius: 162 N/mm$^2$. The resultant material was subjected to an Alcoa cup test and rated excellent/good.

Example 11

A slurry containing 70% SiC, 5% AMP as high temperature binder, and 3% calcium aluminate cement as binder for ambient temperature.

With a water content of 4.5% and a deflocculant additive this mix was self flowing. The following tests were carried out: density, C.C.S. and modulus of rupture tests. The following table shows the results and comparison with competing cement bonded SiC products that are established in market:

| Product/Company | C.C.S. 815° C. | HotMOR | Density 1100 F. | Abrasion CC | SiC cont. |
|---|---|---|---|---|---|
| Ceramite ® CSA | 176 N/mm$^2$ | 29 M/mm$^2$ | 162 lbs/ft$^3$ | n.a. | 75% |
| Resco Vibcast ® 80 | 132 N/mm$^2$ | 37 N/mm$^2$ | 163 lbs/ft$^3$ | <5 cc | 80% |
| Example 11 | 169 N/mm$^2$ | 48 N/mm$^2$ | 163 lbs/ft$^3$ | 2-5 cc | 70% |

In case of example 11 the slurry composition was by weight aluminium-metaphosphate 5%, fume silica 5%, calciumaluminate cement 3%, calcined alumina 12%. The properties of commercially available silicon carbide based ceramics are provided as comparative examples.

Example 12

A larger test shape was filled with 15 lbs of steel-fiber in a form. The voids were filled with 29 lbs of slurry. The slurry contained 61% calcined alumina, 13% fume silica, 13% calcium aluminate cement, 15% AMP and mixed with 15% water which resulted in 37% steel-fiber content in the fired shape. After a setting time of 4 hours and firing at 815° Celsius, a cold crush strength of 132 N/mm$^2$ was noted and a modulus of rupture of 13. It is of note that the slurry contained no aggregate above 45 microns that would have contributed to the strength of the fired article.

The invention claimed is:

1. A refractory composition comprising:
   a plurality of aggregate ceramic particles;
   a binder sintered to said plurality of aggregate ceramic particles, said binder comprising crystalline aluminum orthophosphate distributed in said binder as the result of reaction of aluminum metaphosphate with alumina; and
   a nonfacile additive of calcium aluminate cement, sodium silicate, polyphosphate, or organic salts.

2. The composition of claim 1 wherein said plurality of aggregate ceramic particles comprise bauxite particles.

3. The composition of claim 1 wherein said plurality of aggregate ceramic particles includes at least one of silicon carbide, fumed silica, or mullite.

4. The composition of claim 1 wherein said crystalline aluminum orthophosphate has a crystal structure of berlinite.

5. The composition of claim 1 wherein said crystalline aluminum orthophosphate is devoid of an amorphous glass phase.

6. The composition of claim 1 further comprising steel fiber filler.

7. The composition of claim 1 wherein the composition has a density greater than or equal to 90% of theoretical and a cold crush strength of greater than 100 N/mm$^2$.

* * * * *